United States Patent
Gopinath (10) Patent No.: US 11,166,668 B2
(45) Date of Patent: Nov. 9, 2021

(54) PRE AND POST STENT PLANNING ALONG WITH VESSEL VISUALIZATION AND DIAGNOSTIC SYSTEMS, DEVICES, AND METHODS FOR AUTOMATICALLY IDENTIFYING STENT EXPANSION PROFILE

(71) Applicant: LIGHTLAB IMAGING, INC., Westford, MA (US)

(72) Inventor: Ajay Gopinath, Bedford, MA (US)

(73) Assignee: LightLab Imaging, Inc., Westford, MA (US)

( * ) Notice: Subject to any disclaimer, the term of this patent is extended or adjusted under 35 U.S.C. 154(b) by 1113 days.

(21) Appl. No.: 14/808,901

(22) Filed: Jul. 24, 2015

(65) Prior Publication Data

US 2016/0022208 A1 Jan. 28, 2016

Related U.S. Application Data

(60) Provisional application No. 62/028,711, filed on Jul. 24, 2014.

(51) Int. Cl.
*A61B 5/00* (2006.01)
*A61B 5/107* (2006.01)
(Continued)

(52) U.S. Cl.
CPC .......... *A61B 5/4851* (2013.01); *A61B 5/0066* (2013.01); *A61B 5/02007* (2013.01);
(Continued)

(58) Field of Classification Search
CPC ... A61B 5/4851; A61B 5/6862; A61B 5/0066; A61B 5/1076; A61B 5/02007;
(Continued)

(56) References Cited

U.S. PATENT DOCUMENTS 5,054,492 A 10/1991 Scribner et al.
5,321,501 A 6/1994 Swanson et al.
(Continued)

FOREIGN PATENT DOCUMENTS

JP 2009240359 A 10/2009
JP 2012061086 A 3/2012
(Continued)

OTHER PUBLICATIONS

Chen et al Mis-sizing of stent promotes intimal hyperplasia: impact of endothelial shear and intramural stress, 2011, Am J Physiol Heart Circ Physiol 301: 2011.*
(Continued)

*Primary Examiner* — Serkan Akar
(74) *Attorney, Agent, or Firm* — Lerner, David, Littenberg, Krumholz & Mentlik, LLP (57) ABSTRACT

In part, the disclosure relates to computer-based methods, devices, and systems suitable for pre-stent planning, stent planning and post-stent planning using one or more computing devices. In one embodiment, a method generates one or more stent profiles, such as a target stent profile, that are user configurable during a pre-stent planning stage by selecting one or more frames. The method performs a comparative analysis of the previously set target stent profile relative to a vessel lumen region post stent deployment. The method and related user interfaces can alert a user to move, remove, reposition, or inflate a stent. The location of jailed side branches can also be identified and displayed based upon the comparative analysis. Parameters that change based on the outcome of the stent deployment can be displayed in terms of the predicted parameter value and the value that is measured or determined after stent deployment.

12 Claims, 6 Drawing Sheets

(51) Int. Cl.
*A61B 5/02* (2006.01)
*A61B 5/026* (2006.01)
*A61F 2/95* (2013.01)
*A61B 5/0215* (2006.01)
*A61F 2/82* (2013.01)

(52) U.S. Cl.
CPC ........ *A61B 5/0261* (2013.01); *A61B 5/02154* (2013.01); *A61B 5/1076* (2013.01); *A61B 5/4848* (2013.01); *A61B 5/6862* (2013.01); *A61B 5/7246* (2013.01); *A61B 5/742* (2013.01); *A61B 2560/0475* (2013.01); *A61B 2576/00* (2013.01); *A61F 2/82* (2013.01); *A61F 2/95* (2013.01)

(58) Field of Classification Search
CPC . A61B 5/02154; A61B 5/0261; A61B 5/4848; A61B 5/7246; A61B 5/742; A61B 2560/0475; A61B 2576/00; A61F 2/95; A61F 2/82
See application file for complete search history.

(56) References Cited

U.S. PATENT DOCUMENTS

| | | | |
|---|---|---|---|
| 5,459,570 A | 10/1995 | Swanson et al. | |
| 5,465,147 A | 11/1995 | Swanson | |
| 5,477,858 A | 12/1995 | Norris et al. | |
| 5,488,674 A | 1/1996 | Burt et al. | |
| 5,509,093 A | 4/1996 | Miller et al. | |
| 5,531,227 A | 7/1996 | Schneider | |
| 5,619,368 A | 4/1997 | Swanson | |
| 5,662,109 A | 9/1997 | Hutson | |
| 5,748,598 A | 5/1998 | Swanson et al. | |
| 5,771,895 A | 6/1998 | Slager | |
| 5,784,352 A | 7/1998 | Swanson et al. | |
| 5,797,849 A | 8/1998 | Vesely et al. | |
| 5,965,355 A | 9/1999 | Swanson et al. | |
| 5,989,189 A | 11/1999 | LeBlanc et al. | |
| 6,111,645 A | 8/2000 | Tearney et al. | |
| 6,134,003 A | 10/2000 | Tearney et al. | |
| 6,148,095 A | 11/2000 | Prause et al. | |
| 6,160,826 A | 12/2000 | Swanson et al. | |
| 6,191,862 B1 | 2/2001 | Swanson et al. | |
| 6,208,883 B1 | 3/2001 | Holupka et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,706,004 B2 | 3/2004 | Tearney et al. | |
| 6,879,851 B2 | 4/2005 | McNamara et al. | |
| 6,891,984 B2 | 5/2005 | Petersen et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,397,935 B2 | 7/2008 | Kimmel et al. | |
| 7,414,779 B2 | 8/2008 | Huber et al. | |
| 7,415,049 B2 | 8/2008 | Flanders et al. | |
| 7,593,559 B2 | 9/2009 | Toth et al. | |
| 7,619,646 B2 | 11/2009 | Freifeld et al. | |
| 7,625,366 B2 | 12/2009 | Atlas | |
| 7,729,746 B2 | 6/2010 | Redel et al. | |
| 7,813,609 B2 | 10/2010 | Petersen et al. | |
| 7,848,791 B2 | 12/2010 | Schmitt et al. | |
| 7,916,387 B2 | 3/2011 | Schmitt et al. | |
| 7,935,060 B2 | 5/2011 | Schmitt et al. | |
| 8,116,605 B2 | 2/2012 | Petersen et al. | |
| 8,206,377 B2 | 6/2012 | Petroff | |
| 8,298,147 B2 | 10/2012 | Huennekens et al. | |
| 8,325,419 B2 | 12/2012 | Schmitt | |
| 8,358,461 B2 | 1/2013 | Huber et al. | |
| 8,412,312 B2 | 4/2013 | Judell et al. | |
| 8,449,468 B2 | 5/2013 | Petersen et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,687,201 B2 | 4/2014 | Adler | |
| 8,786,336 B1 | 7/2014 | Schmitt | |
| 8,831,321 B1 | 9/2014 | Elbasiony | |
| 8,948,228 B2 | 2/2015 | Adler | |
| 8,953,911 B1 | 2/2015 | Xu et al. | |
| 2002/0115931 A1 | 8/2002 | Strauss et al. | |
| 2002/0161351 A1 | 10/2002 | Samson et al. | |
| 2003/0200120 A1* | 10/2003 | Binkert | G06F 19/3481 705/3 |
| 2005/0201662 A1 | 9/2005 | Petersen et al. | |
| 2005/0238067 A1 | 10/2005 | Choi | |
| 2006/0095065 A1 | 5/2006 | Tanimura et al. | |
| 2006/0165270 A1 | 7/2006 | Borgert et al. | |
| 2006/0187537 A1 | 8/2006 | Huber et al. | |
| 2006/0203859 A1 | 9/2006 | Cable et al. | |
| 2006/0241465 A1 | 10/2006 | Huennekens et al. | |
| 2006/0244973 A1 | 11/2006 | Yun et al. | |
| 2007/0167710 A1 | 7/2007 | Unal et al. | |
| 2007/0293932 A1* | 12/2007 | Zilla | A61F 2/06 623/1.11 |
| 2008/0100612 A1 | 5/2008 | Dastmalchi et al. | |
| 2009/0027051 A1 | 1/2009 | Stuber et al. | |
| 2009/0174931 A1 | 7/2009 | Huber et al. | |
| 2009/0204134 A1* | 8/2009 | Kassab | A61B 5/053 606/159 |
| 2009/0226063 A1* | 9/2009 | Rangwala | G06T 5/008 382/128 |
| 2009/0306520 A1 | 12/2009 | Schmitt et al. | |
| 2010/0076320 A1 | 3/2010 | Petersen et al. | |
| 2010/0094127 A1 | 4/2010 | Xu | |
| 2011/0071404 A1* | 3/2011 | Schmitt | A61B 5/0066 600/479 |
| 2011/0101207 A1 | 5/2011 | Schmitt | |
| 2011/0157686 A1 | 6/2011 | Huber et al. | |
| 2011/0190586 A1 | 8/2011 | Kemp | |
| 2011/0228280 A1 | 9/2011 | Schmitt et al. | |
| 2011/0257545 A1 | 10/2011 | Suri | |
| 2012/0310081 A1 | 6/2012 | Adler et al. | |
| 2012/0238869 A1 | 9/2012 | Schmitt et al. | |
| 2012/0250028 A1 | 10/2012 | Schmitt et al. | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0051728 A1 | 2/2013 | Petroff | |
| 2013/0072805 A1 | 3/2013 | Schmitt et al. | |
| 2013/0303888 A1 | 11/2013 | Deladi et al. | |
| 2013/0310698 A1 | 11/2013 | Judell et al. | |
| 2014/0018669 A1 | 1/2014 | Xu | |
| 2014/0024931 A1 | 1/2014 | Winston et al. | |
| 2014/0094697 A1* | 4/2014 | Petroff | A61B 5/0066 600/427 |
| 2014/0100449 A1 | 4/2014 | Begin et al. | |
| 2014/0114182 A1 | 4/2014 | Petersen et al. | |
| 2014/0142427 A1 | 5/2014 | Petroff | |
| 2014/0142432 A1 | 5/2014 | Hutchins et al. | |
| 2014/0142436 A1 | 5/2014 | Hutchins et al. | |
| 2014/0187929 A1 | 7/2014 | Schmitt et al. | |
| 2014/0218742 A1 | 8/2014 | Adler | |
| 2014/0249407 A1 | 9/2014 | Adler et al. | |
| 2014/0268167 A1 | 9/2014 | Friedman et al. | |
| 2014/0276011 A1 | 9/2014 | Schmitt et al. | |
| 2014/0309536 A1 | 10/2014 | Douk et al. | |
| 2014/0379269 A1* | 12/2014 | Schmitt | A61B 5/6852 702/19 |
| 2015/0153157 A1 | 6/2015 | Schmitt et al. | |

(56) References Cited

U.S. PATENT DOCUMENTS

| | | |
|---|---|---|
| 2015/0119707 A1 | 7/2015 | Schmitt |
| 2015/0192405 A1 | 7/2015 | Schmitt |

FOREIGN PATENT DOCUMENTS

| | | |
|---|---|---|
| JP | 2012505669 A | 3/2012 |
| JP | 2013505782 A | 2/2013 |
| JP | 2014500043 A | 1/2014 |
| WO | 2006076409 | 7/2006 |
| WO | 2007002685 | 1/2007 |
| WO | 2010045386 A1 | 4/2010 |
| WO | 2011038044 | 3/2011 |
| WO | 2011038044 A2 | 3/2011 |
| WO | 2012042413 A1 | 4/2012 |
| WO | 2013042231 A1 | 3/2013 |
| WO | 2014092755 | 6/2014 |
| WO | 2014092755 A1 | 6/2014 |

OTHER PUBLICATIONS

International Search Report and Written Opinion of the International Searching Authority for International application No. PCT/US2015/042083 mailed from the International Searching Authority dated Oct. 21, 2015 (9 pages).

International Preliminary Report on Patentability for International application No. PCT/US2015/042083 issued by the International Bureau of WIPO dated Jan. 24, 2017 (1 page).

International Search Report and Written Opinion o the International Search Authority for International patent application No. PCT/US2015/042083 dated Oct. 21, 2015 (9 pages).

Bonnema et al., "An automatic algorithm for detecting stent endothelialization from volumetric optical coherence tomography datasets", Physics in Medicine and Biology, 53:12, Jun. 21, 2008, pp. 3083-3098.

Takano et al., "Evaluation by Optical Coherence Tomography of NeointimalCoverage of Sirolimus-Eiuting Stent Three Months After Implantation", American Journal of Cardiology, 99:8, Apr. 14, 2007, pp. 1033-1038.

Unai et al., "Stent implant follow-up in intravascular optical coherence tomography images", Int J Cardiovasc Imaging, DOI 10.1007/s10554-009-9508-4, published online Sep. 24, 2009, 8 pgs.

Xu et al., "Characterization of atherosclerosis plaques by measuring both backscattering and attenuation coefficients in optical coherence tomography", Journal of Biomedical Optics, 13:3, May/Jun. 2008, 8 pgs.

* cited by examiner

PRE AND POST STENT PLANNING ALONG WITH VESSEL VISUALIZATION AND DIAGNOSTIC SYSTEMS, DEVICES, AND METHODS FOR AUTOMATICALLY IDENTIFYING STENT EXPANSION PROFILE

CROSS-REFERENCE TO PRIOR APPLICATIONS

This application claims priority to and the benefit of U.S. Provisional Patent Application No. 62/028,711, filed on Jul. 24, 2014, the entire contents of which are hereby incorporated by reference.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a user to diagnose as well as monitor the progression of coronary artery disease.

OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be deployed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An under expanded stent may fail to restore normal flow. Clearly, after a stent is installed, stent over and under expansion of the stent can result in various problems.

There are other challenges associated with stent placements and related procedures. Visualizing a stent deployment relative to the wall of a blood vessel using an angiography system is challenging to undertake by inspection.

Further, reviewing images manually to determine stent position on a per image basis is also prone to error. A need therefore exists for systems, methods, and devices that facilitate evaluating the expansion of a vessel using a stent or the stent itself using intravascular diagnostic information.

The present disclosure addresses these challenges and others.

SUMMARY

In part, the disclosure relates to systems, methods and devices to evaluate a deployed stent in a blood vessel relative to one or more planning stages and profiles obtained with respect to the blood vessel or stent. The profiles and information relating to the blood vessel or stent can be obtained using an intravascular data collection system and related probes, such as an optical coherence tomography (OCT) or intravascular ultrasound (IVUS) or other intravascular data collection modalities. Further, the disclosure provides an automated method for a user, such as a clinician or other person, to evaluate whether a stent placed in a blood vessel has been expanded to a suitable level such as a substantially optimal level or other suitability metrics. These metrics can be user specified in one embodiment. If the stent is overexpanded, improperly positioned, or is jailing sidebranches, these states can also be evaluated using the methods and system described herein.

In part, the disclosure relates to a method of evaluating stent deployment in a blood vessel. The method includes generating, using one or more computing devices, a representation of a segment of the blood vessel using a first set of intravascular data obtained with respect to the blood vessel; receiving a selection of a distal or first reference relative to a representation of a segment of the blood vessel; receiving a selection of a proximal or second reference relative to a representation of a segment of the blood vessel; generating a target stent profile, using one or more computing devices, based upon the distal reference and the proximal reference; generating, using one or more computing devices, a blood vessel lumen profile after deployment of a stent in the blood vessel; comparing the target stent profile to one or more regions of the blood vessel lumen profile; and generating an output using a user interface including one or more differences resulting from comparing the target stent profile to the one or more regions. In one embodiment, the generating of an output includes displaying one or more outputs indicative of a correlation or goodness of fit between the target stent profile and the one or more regions of the blood vessel lumen profile. In one embodiment, the first reference may be the distal reference such as a user selected distal frame and the second reference may be the proximal reference such as a user selected proximal frame and vice versa.

The method may include displaying an indicator of a jailed sidebranch based upon one or more sidebranches being undetected when comparing the target stent profile to one or more regions of the blood vessel lumen profile. In one embodiment, the one or more outputs are a visual depiction of the target stent profile overlapping one or more regions of the blood vessel lumen profile. In one embodiment, the one or more outputs is a comparative metric of a change in a parameter measured or calculated relative to the segment of the blood vessel. In one embodiment, the parameter is selected from the group consisting of a fractional flow reserve, a flow rate, a vascular resistance ratio, a virtual fractional flow reserve, a simulated fractional flow reserve, a measured fractional flow reserve, and a pressure measurement.

In one embodiment, the method includes generating, using one or more computing devices, a blood vessel lumen profile after deployment of a stent in the blood vessel comprises generating a representation of a segment of the blood vessel using a second set of intravascular data obtained with respect to the blood vessel. In one embodiment, the first set of intravascular data is obtained during a first optical coherence tomography imaging session. In one embodiment, the second set of intravascular data is obtained during a second optical coherence tomography imaging session.

In one embodiment, the method includes generating and displaying a difference between the post-stent lumen profile and the pre-stent target profile or a value correlated with the difference on a per frame or per segment basis. In one embodiment, the method includes detecting one or more side branches in the blood vessel. In one embodiment, the method includes adjusting a shape of the target stent profile on a per side branch basis. In one embodiment, the method includes the step of adjusting the shape includes stepping up the stent profile at each detected side branch if a distal reference diameter is less than the proximal reference diameter. In one embodiment, the method includes the step of adjusting the shape includes stepping down the stent profile at each detected side branch if a distal reference diameter is greater than the proximal reference diameter.

In part, the disclosure relates to a processor-based stent deployment evaluator or evaluation system. The system or evaluator includes one or more memory devices; and a computing device in communication with the memory device, wherein the memory device comprises instructions executable by the computing device to cause the computing device to: generate a target stent profile in response to one or more user selections from a user interface, the user interface displaying a first representation of the blood vessel, the user selections comprising a proximal reference and a distal reference; generate a second representation of the blood vessel after stent deployment and display the second representation; and display one or more parameters relative to the second representation of the blood vessel, the one or more parameters indicative of the deployed stent being underexpanded, overexpanded, or overlapping a sidebranch.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

In part, the disclosure relates to computer-based methods, devices, and systems suitable for pre-stent planning, stent planning and post-stent planning using one or more computing devices. One or more devices can display one or more user interfaces and intravascular data or other information derived from such data. The intravascular data can be obtained using IVUS or OCT based data collection systems and probes or other imaging modalities. The methods can be implemented using one or more computing devices and memory storages that receive intravascular data and user inputs via a graphic user interface (GUI) and include one or more image processing and frame selection software components. The computing devices can be microprocessors, ASICs or other processors suitable for use with an intravascular imaging system.

Figure 1:
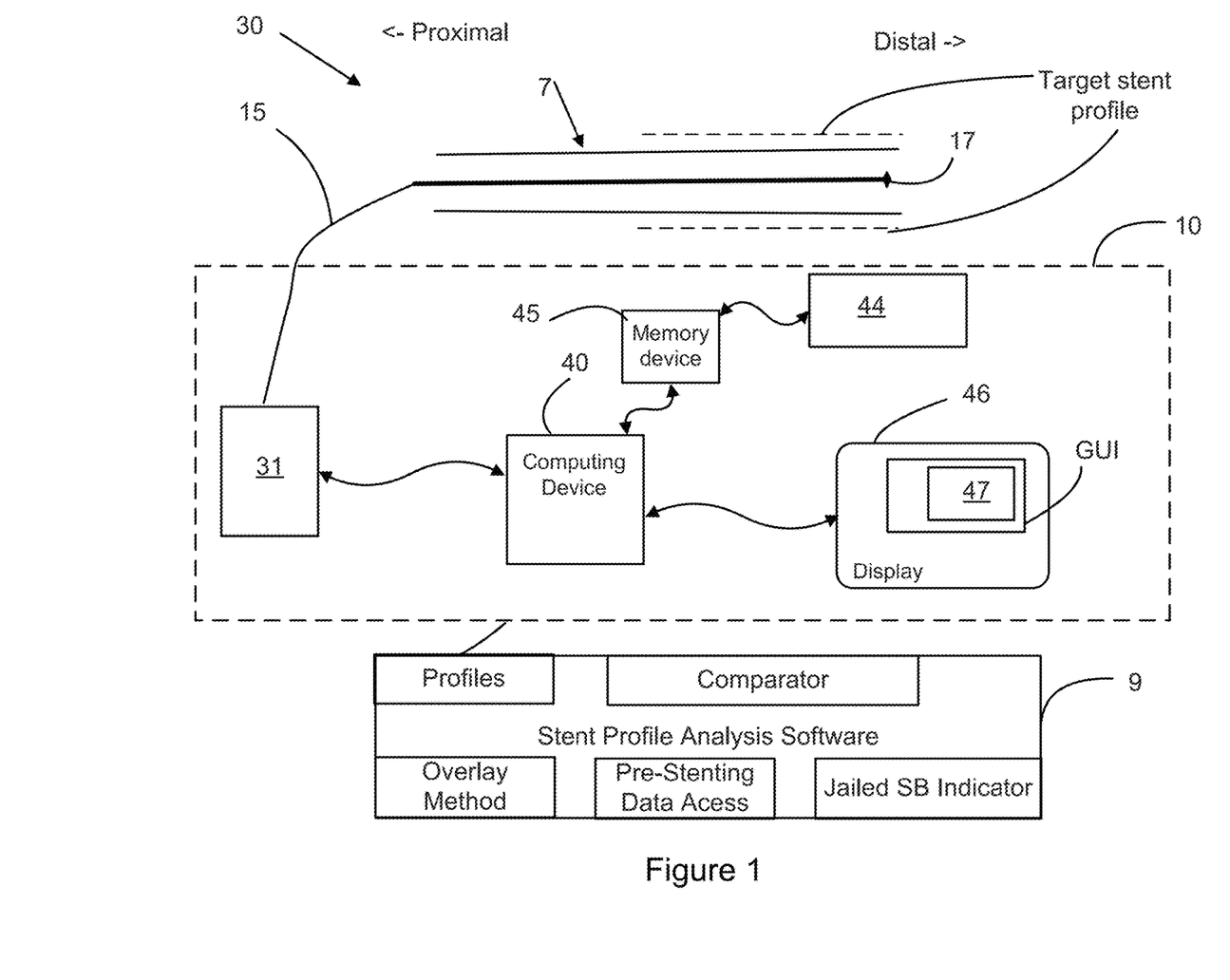
FIG. 1 is a schematic diagram of data collection system and a data collection probe in accordance with an illustrative embodiment of the disclosure.

As shown in FIG. 1, a probe 7 is shown prior to or after insertion in a blood vessel. The probe 7 can include other imaging modalities in addition to or in lieu of OCT such as ultrasound in one embodiment. The probe 7 is in optical communication with an OCT system 10 or other imagining system such as an IVUS system. The OCT system or subsystem 10 that connects to probe 7 via an optical fiber 15 can include a light source such as a laser, an interferometer having a sample arm and a reference arm, various optical paths, a clock generator, photodiodes, and other OCT system components.

Figure 5:
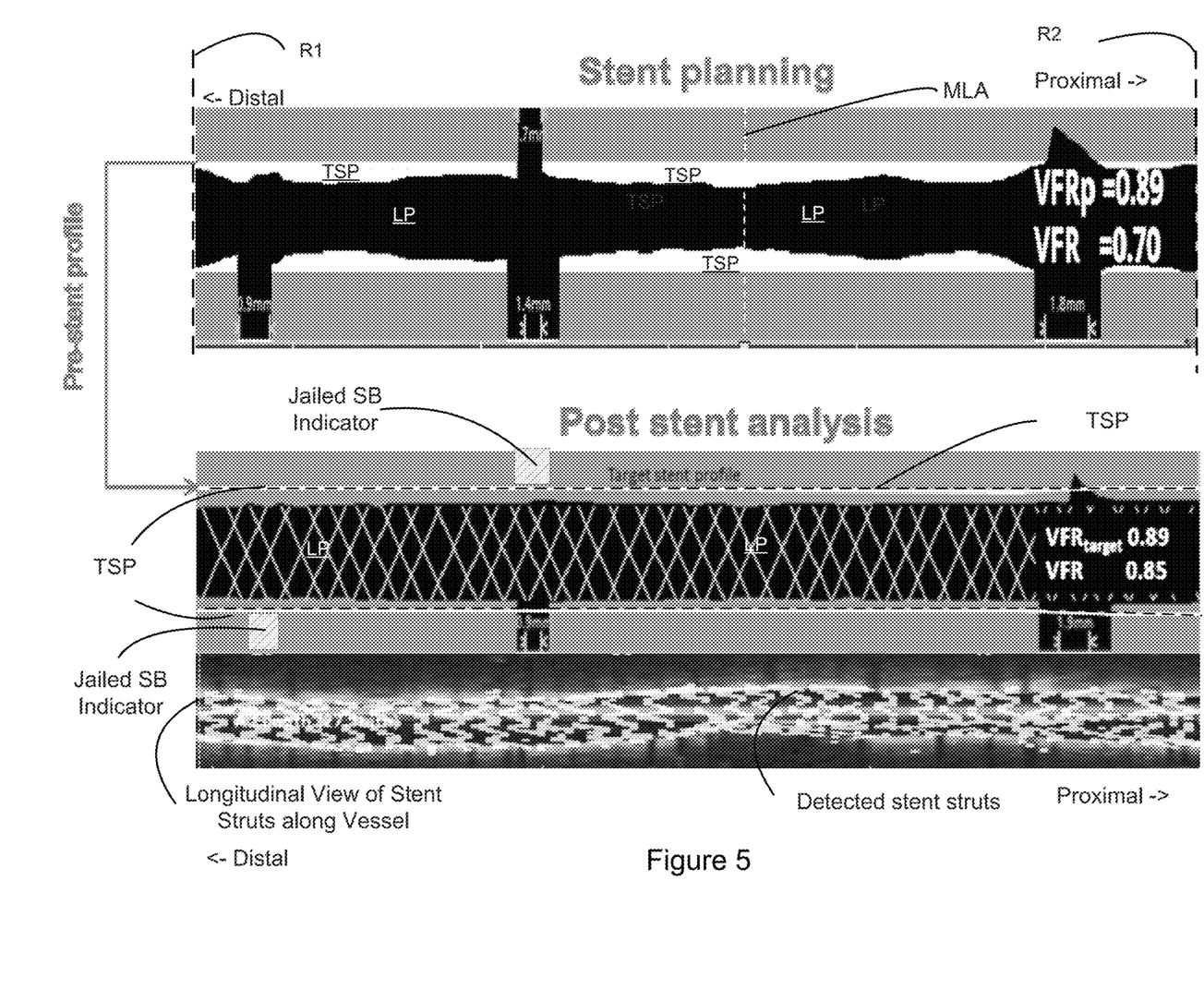
FIG. 5 is a schematic diagram of the stent planning schematic diagram of FIG. 3 in the top portion of the figure, which provides the pre-stent target profile as an input to the post-stent comparative analysis in accordance with an illustrative embodiment of the disclosure.

The system 10 includes stent profile analysis software. The software can be stored as a non-transitory instructions one or more memory devices such as memory device 45 and executed by one or more computing devices such as computing device 40. The stent profile analysis software can include one or more profiles such as target profiles generated by a user, a comparator or other comparison software routine for compare pre and post stent profiles or other profiles. The stent profile analysis software 9 can include an overlay method suitable to superimpose the image of a deployed stent relative to a target profile or to otherwise overlay one or more pre or post stent profiles. The software 9 can also include a jailed sidebranch indicator software module that identifies when a sidebranch and a stent overlap. The software 9 can also compare FFR, VRR, and other values determined with respect to a first and second intravascular data collection session also referred to as a pullback. The stent profile analysis software 9 can include the software components and others shown in FIG. 1 to implement the methods and features described herein. The software 9 can also be part of a pipeline of other intravascular data processing modules as shown in FIG. 5.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for stent visualization, stent malapposition detection, and pullback data collection as discussed below.

In one embodiment, the computing device 40 includes or accesses software modules or programs 44, such as a side branch detection module, a guide wire detection module, a lumen detection module, a stent detection module, a median mask clearing module, an intensity averaging module, a stent malapposition detection module, a stent planning module, a stent analysis module, FFR measurement module, VRR measurement module, and other software modules. The software modules or programs 44 can include an image data processing pipeline or component modules thereof and one or more graphical user interfaces (GUI). An exemplary image processing pipeline 50 for transforming collected OCT data into two dimensional and three dimensional views of blood vessels and stents is depicted in FIG. 5. The image data processing pipeline or any of the methods described herein are stored in memory and executed using one or more computing devices such as a processor, device, or other integrated circuit.

As shown, in FIG. 1, a display 46 can also be part of the system 10 for showing information 47 such as cross-sectional and longitudinal views of a blood vessel generated using collected OCT data. This OCT-based information 47 can be displayed using one or more graphic user interface(s) (GUI). In addition, this information 47 can include, without limitation, cross-sectional scan data, longitudinal scans, diameter graphs, target stent profiles, proximal reference values, distal reference values, FFR values before stenting and after stenting or the underlying distance measurements obtained using an OCT or IVUS system and data collection probe. The computing device 40 can also include software or programs 44, which can be stored in one or more memory devices 45, configured to identify sidebranches, underinflated stent regions, and other stent deployment measured or calculated values and other blood vessel features such as with text, arrows, color coding, highlighting, contour lines, or other suitable human or machine readable indicia.

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in the figures. The images of the blood vessel generated using the distances measurements obtained from the OCT system provide information about the blood vessel and objects disposed therein.

In one embodiment, a method generates one or more stent profiles, such as a target stent profile, that are configurable by a user during a pre-stent planning stage by selecting one or more reference frames. The method performs a comparative analysis of the previously set target stent profile relative to a vessel lumen region post stent deployment. The method and related user interfaces can alert a user to move a stent, remove a stent, reposition a stent, or inflate a stent. The location of jailed side branches can also be identified and displayed based upon the comparative analysis. Parameters that change based on the outcome of the stent deployment can be displayed in terms of the predicted parameter value and the value that is measured or determined after stent deployment. These parameters can provide an indication to a user that a stent needs to be moved or inflated as a result of the values of the parameters being less than the target parameters from the planning stage.

In part, the disclosure relates to computer-based methods, systems and devices for visualizing stents. In one embodiment, the disclosure relates to methods to evaluate the expansion of a stented vessel and whether further expansion is needed or if stent repositioning is needed. These methods of evaluation can include displaying one or more views of a stent in various states such as an expanded state relative to the blood vessel and comparing the imaged stent relative to one or more selected stent profiles. In one embodiment, the method is performed automatically. The methods of the disclosure can be implemented using software such as stent profile analysis software which can include stent planning software and lesion preparation software (or vice versa).

A stent may be selected for deployment using OCT, IVUS, angiography or other probe data obtained relative to the unstented vessel segment and then subsequently compared to stented blood vessel. The stented and unstented stages of stent planning can be subsequently displayed longitudinally or in a cross-sectional view in expanded or unexpanded state as a part of a one or more graphic user interface(s) (GUI). Such an interface can include one or more views of a blood vessel generated using distance measurements obtained using an OCT system, IVUS system, angiography system or other data collection systems.

In one embodiment, the method includes receiving a target stent expansion profile set by a user in the pre-stent planning phase. The method can also compare the target profile to one or more vessel lumen regions after stent deployment. The method provides an accurate process to compare the target stent profile and the current expansion of the stent. For Bio Re-absorbable Stents (BRS), where the user gets a single attempt to expand the stent post-deployment, indicating the region where the stent needs to be expanded, also helps determine where to inflate the balloon and to select the size of the balloon for post stent expansion. Thus, one pullback is performed with an imaging prove to understand the lumen environment which is compared to the results of a second pullback post-stenting. The second pullback can be performed just after stenting so that further inflation or reposition or removal can be performed. In one embodiment, a stent plan can be entered via a GUI and stored in memory for use and comparison to other intravascular data and images.

A stent plan can include a first location such as a start frame and a second location such as an end frame. A stent plan can include a plurality of stent diameters. In one embodiment, the stent plan includes a first and a second location along an imaged vessel and the stent diameter at the first and the second location. The stent plan can include a plurality of frames wherein the frames are generated using intravascular optically or acoustically measured data and parameters such as optical coherence tomography and IVUS data and parameters. The frames can include longitudinal, cross-sectional, or other views or images or data obtained relative to a blood vessel at one or more time periods. As an example, a first time period can include a first pullback during which the vessel is imaged. Similarly, a second time period can include a second pull back during which the vessel is imaged. In one embodiment, in addition to a first frame and a second frame, the stent plan can include the stent diameter at one or more frames such as the first frame and the second frame or frames in between the first and second frames and combinations thereof. In one embodiment, the stent diameter for each frame including or subsequent to the first and second frames is included in the stent plan.

Figure 2:
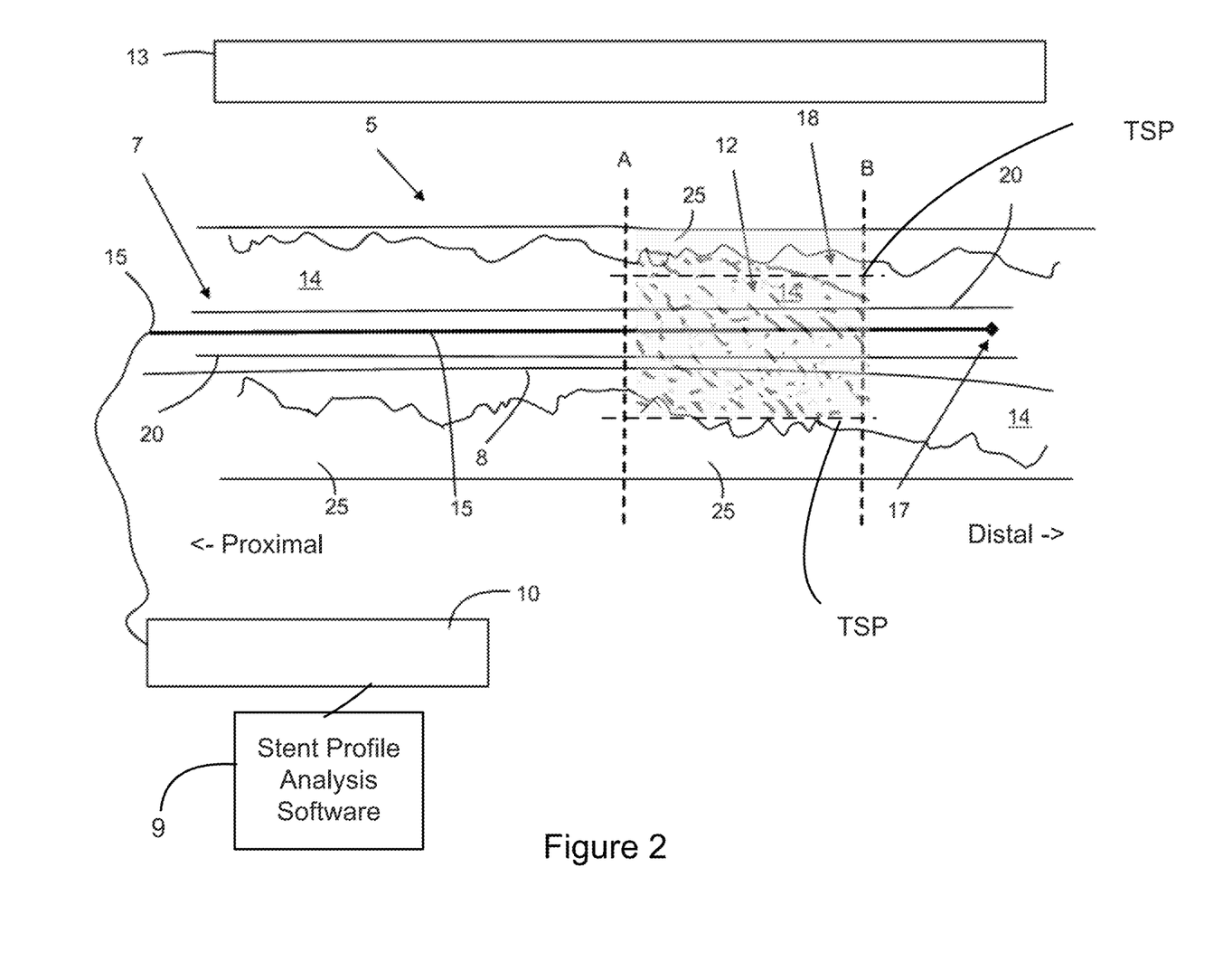
FIG. 2 is a schematic diagram of a data collection system and a data collection probe positioned relative to a stent in a blood vessel in accordance with an illustrative embodiment of the disclosure.
Figure 3:
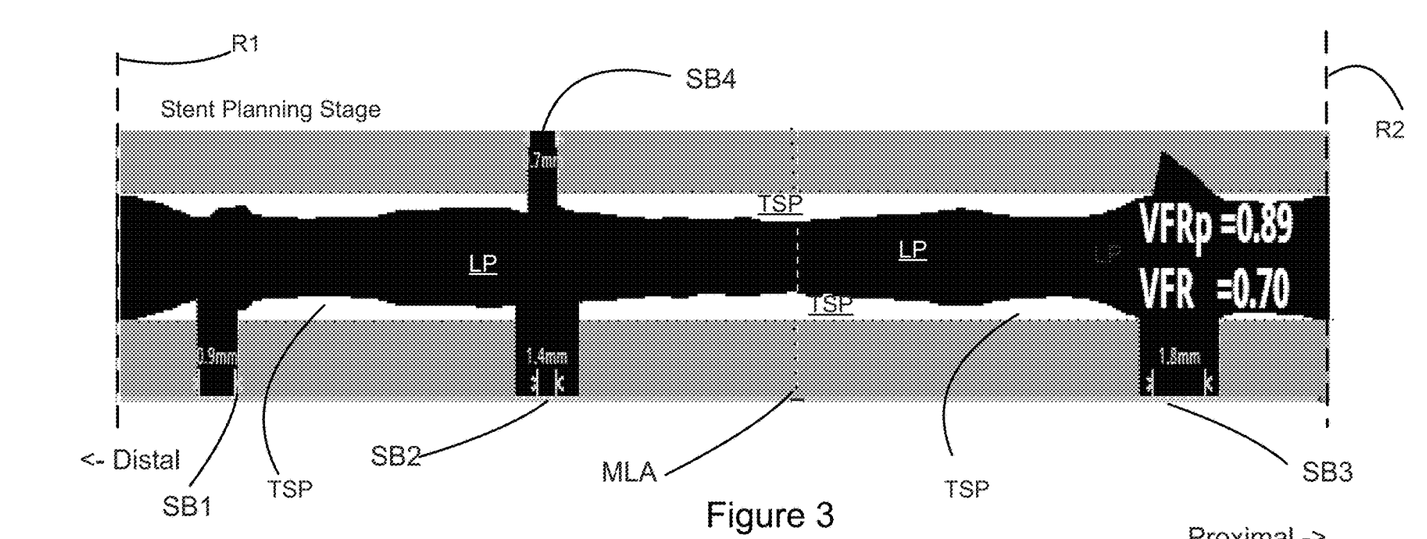
FIG. 3 is a schematic diagram of a lumen profile of an intravascularly imaged blood vessel that shows four side branches, a lumen profile (LP), and a computing device generated target stent profile (TSP) according to an illustrative embodiment of the disclosure.
Figure 4:
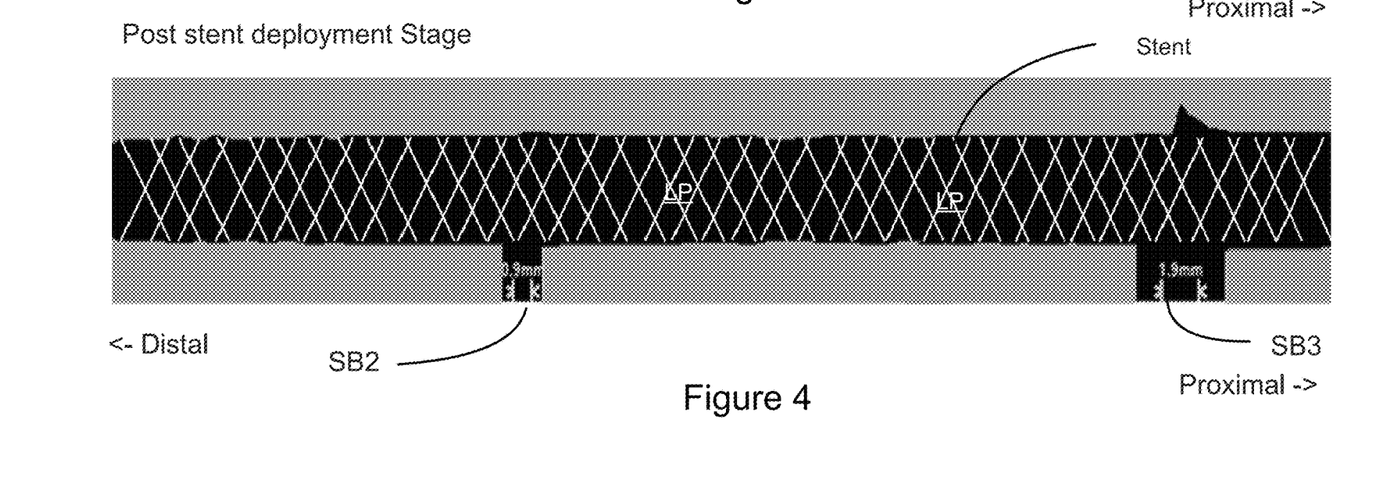
FIG. 4 is a schematic diagram of the lumen profile of the blood vessel after the stent has been deployed relative to a LP according to an illustrative embodiment of the disclosure. As shown, two side branches have been blocked after stenting and only two were detected after a second pullback.

Optical coherence tomography (OCT) is an imaging modality that uses an interferometer to obtain distance measurements relative to a sample such as, for example, a blood vessel or objects disposed therein. Intravascular Ultrasound or IVUS is an ultrasound or acoustic wave based imaging modality. One or both of these can be combined in an intravascular data collection probe. As shown in FIG. 2, a blood vessel 5 can be imaged using a data collection probe 7. A guidewire 8 can be used to introduce the probe 7 into the blood vessel 5 as shown in FIG. 2. Examples of blood vessel images or data generated from data collected with such as probe are shown in FIGS. 3, 4 and 5.

The data collection probe 7 can be introduced and pulled back along a length of a blood vessel 5 while collecting data. As the optical fiber is retracted (pulled-back) along the length of the vessel, a plurality of scans or OCT data sets are collected as the probe or a portion thereof rotates. This is referred to as a pullback in one embodiment. These data sets can be used to identify regions of interest such as a stenosis or a deployed stent such as stent 12. In one embodiment, a first pull back is performed pre-stent deployment and a second pullback is after stent deployment. Angiography data can be generated relative to the imaged vessel during both the first and second pullbacks. Regions of interest and parameters such as vascular resistance ratio, FFR, lumen area, lumen profiles, and other parameters can be compared between the first and second pullbacks.

In one embodiment, the data collection probe 7 is an OCT probe configured for use with an OCT system 10 that includes an interferometer and a data processing system. The distance measurements collected using the OCT probe 7 can be processed to generate frames of image data such as cross-sectional views or longitudinal views (L-mode views) of the blood vessel. For clarity, a cross-sectional view can include without limitation a longitudinal view. These images can be processed using one or more image data processing modules or stages such as outlined herein.

For a blood vessel 5 as shown in FIG. 2, which includes a stent 12 disposed in the lumen 14 of the blood vessel various types of data collection probes and related OCT systems can be used. In one embodiment, the OCT system 10 includes a processor, memory, or other components configured to execute various data processing stages or modules. These stages or modules operate upon and transform image data. These modules or stages can include a stent detection software component and a stent malapposition detection component. A given stent and components thereof can be visualized to include an indicia or measurement of the degree of contact or lack of contact between one or more stent struts, which are components of the stent, and the wall of a blood vessel. One area showing a degree of stent underinflation with respect to stent 12 and wall 26 is shown in region 18. The display of FIGS. 4 and 5 can be used as a diagnostic by a user to further inflate a stent in such a scenario. Additional details relating to these features are described herein.

As shown in FIG. 2, for a given blood vessel, the walls of the vessel define a lumen in which blood flows. X-ray based imaging modalities such as provided by angiography system 13 can be used to image blood vessels and facilitate stent deployment or stent visualization. In addition, as described herein a probe 7 suitable for insertion in a blood vessel 5 can be used to generate images of sections of a given blood vessel. Areas of stenosis or previously deployed stents such as stent 12, which is disposed in lumen 14, can be viewed using various cross-sectional and three-dimensional views of a blood vessel obtained with an OCT system and associated data collection probe.

FIG. 2 is a high level schematic diagram depicting a data collection probe and an OCT system 10 suitable for performing side branch detection, lumen detection, guide wire detection and various other processes. The OCT system 10 can include a suitable light source that satisfies the coherence and bandwidth requirements of the applications and data collection described herein. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 14 such as an arterial lumen. The probe 7 can include a rotating or slidable fiber 15 that directs light forward into the lumen 14 or at a direction perpendicular to the longitudinal axis of the fiber 15. As a result, in the case of light that is directed from the side of the probe as the fiber 15 rotates, OCT data is collected with respect to the walls 25 of the blood vessel 5. The walls of the blood vessel 25 define a lumen boundary. This lumen boundary can be detected using the distance measurements obtained from the optical signals collected at the probe tip 17 using a lumen detection software component or module. In lieu of a fiber, an ultrasound transducer can be used suitable for collecting IVUS signals with regard to the vessel wall and one or more stents.

The lumen detection software can include one or more steps. For example, to perform lumen detection in one embodiment a filter or other image processing device can be applied to a two dimensional image to detect edges in the images, the edges indicative a lumen boundary. In another embodiment, a scan line based approach is used. During one or more pullbacks, optical or ultrasound signals are collected as scan lines with respect to a blood vessel and one or more stents disposed in the lumen of the vessel. In one embodiment, the lumen detection software executing a computing device generates one or more images from the set of scan lines using a computing device.

Further, lumen detection can include generating a binary mask of the vascular image using the computing device, wherein the binary mask is generated using an intensity threshold. As another step, a plurality of scan lines are defined in the binary mask. With regard to each scan line of the plurality of scan lines, in one embodiment, a region is identified as lumen boundary tissue thereon. Contour segments of the boundary are identified in based on the presence of a region of lumen boundary tissue. In one embodiment, the method identifies neighboring contour segments. The lumen boundary detection method can also include interpolating missing contour data between neighboring contour segments. As a result, in one embodiment, the neighboring contour segments and the interpolated missing contour data define the lumen boundary.

As shown in FIG. 2, the probe tip 17 is positioned in the lumen 14 such that it is distal to a stented region of the blood vessel 5, which is bounded by dotted lines A, B. The probe tip 17 is configured to transmit light and receive backscattered light from objects, such as for example stent 12, and the wall 25 of the blood vessel 5. The probe tip 17 and the rest of the data collection probe 7 are pulled through the lumen 14 such that the tip passes through the stented region defined by lines A, B. The target stent profile or TSP generated in response to the user selected reference frames is shown in between lines A and B of the deployed stent. The target stent profile is generated using one or more method described herein which includes one or more user provided reference frames or other selections relative to identifying a section of a blood vessel as inputs. In one embodiment, the target stent profile is automatically placed over or overlaid upon the region of the lumen profile that corresponds to the detected stent struts such as shown in FIG. 5.

Accordingly, in part, the disclosure relates to software-based methods and related systems and devices suitable for evaluating and depicting information regarding a blood vessel, a stent or other vascular information of interest. The OCT data can be used to generate 2-D views such as cross-sectional and longitudinal views of a blood vessel before or after an initial stent deployment or corrective stent related procedure. The OCT data obtained using a data collection probe and various data processing software modules can be used to identify, characterize, and visualize a stent and/or one or more properties relating to the stent and/or the lumen in which it is disposed.

Further, once such a two-dimensional or a three-dimensional image has been generated or the underling measurements are available in a data store, such as a database or memory device, measurements can be obtained relative to the blood vessel and stent to further enhance diagnosis efforts. For example, measurements relating to a stent such as a degree of stent profile misaligned can be generated automatically using OCT data without a need for a user to engage in calculations.

In one embodiment, as shown in FIG. 2, the angiography system 13 can be used to obtain a high level view of the blood vessel of interest. This step can precede or occur simultaneously with the pullback of the rotatable OCT probe. As an example of such a procedure, once the software has automatically determined and displayed stent profile and stent profile mismatches such that there is a correlation or a lack thereof to a user, the user may elect to use a balloon to further inflate a deployed stent. The balloon can be positioned with the aid of the angiography system 13 and used to inflate the balloon to change the stent state and reduce the level of underinflation. Another OCT pullback can be performed to review an installed stent in one embodiment. Stent detection, stent position and lumen detection can be performed using a plurality of software modules arranged in an image data processing pipeline with images or OCT data as the inputs.

In the stent planning phase, a target stent expansion profile (alternatively referred to as a TSP or target stent profile) is determined using a computing device such as a processor or microprocessor in electrical communication with an intravascular data collection system. The target stent profile is generated based on one or more user selections such as the user selected reference regions in the proximal and distal regions as shown in FIG. 3. By setting a proximal and distal reference, with associated lumen diameters, the user defines a segment that is the target region of the vessel for stenting. In FIG. 3, using the lumen diameter in the proximal and distal reference regions and the intermediate branch diameter, an optimal stented taper is generated that connects the proximal and distal reference region. The vertical dotted line in FIG. 3 is a minimum lumen area value or MLA.

The stent profile is a constant in a given segment between the reference frames. The profile across a branch is linearly interpolated. That is, the physiological tapering of the blood vessel along its length and the proximal and distal references are used to generate upper and lower boundaries for the target stent profile. If the reference frames are in the same segment (i.e. no branch in between them) then the stent profile is a linear interpolation between the two reference frames.

In one embodiment, the method adjusts the geometric shape of the profile by stepping up the target stent profile at each branch point going from distal to proximal if the distal reference diameter is less than the proximal reference diameter. If the distal reference diameter is greater than the proximal reference diameter, then the method will step down the target stent profile at each segment going from distal to proximal. In this way, a user selection of reference endpoints and the tapering properties of a vessel and the associated flow and other changes due to sidebranches is taken into account and modelled to understand the predicted changes that stenting will cause.

If the distal and proximal reference frames are in the same segment, the stent profile is a linear interpolation between the distal and proximal reference frames. In one embodiment, the method to determine a target stent profile in response to one or more user selected reference frames is as follows.

Determining the total number of side branches between the reference frames is: N For example in FIG. 3, four (N=4) side branches are shown between the most distal and proximal frame of the segment shown. One side branch is at the top of the lumen and three are disposed at the bottom.

exp=2.3 is the scaling exponent. In one embodiment, the exp values ranges from greater than or equal to about 2 to less than or equal to about 3. This exp value describes scaling of the taper of the segment between the user selected reference frames. Selection of the best value of exp is based on statistical analysis of OCT and angiographic image databases in which the tapering of the vessels and the branch diameters of those vessels are measured. In normal subjects the exp value ranges from about 2.2 to about 2.7.

The difference between the proximal and distal reference diameter is:

$$\Delta = d_{prox}^{exp} - d_{dist}^{exp}$$

$d_{prox}$ is the diameter of the proximal reference frame and $d_{dist}$ is the distal reference frame diameter.

$$\Delta = \sum_{n}^{N} \partial_n$$

$\partial_n$ is the increment of stent segment at the nth branch (to be calculated)

Segment increment at each branch is proportional to the diameter of the branch raised to the scaling law exponent.

$$\partial_n \propto BranchD_n^{exp}$$

$$\partial_n = \frac{BranchD_n^{exp} * \Delta}{\sum_{n}^{N} BranchD_n^{exp}}$$

Diameter of stent in segment $n+1$:

$$SegDia_{n+1} = \sqrt[exp]{SegDia_n^{exp} + \partial_n}$$

The segment diameter above provides a delta measurement by which the boundary of an upper and lower taper of the target stent profile undergoes a stepwise change in the amount of such of delta measurement as the tapered boundaries are generated across the vessel segment. In the pre-stent deployment or stent planning phase, the target stent expansion profile (pre-stent target) will set a target for the user. The user interface will present stent size choices to assist them in choosing a suitably sized stent given the target profile.

After the stent has been deployed, the stent detection algorithm locates the stented lumen region. The lumen profile in the stented region is compared with the pre-stent target. Any over or under expansion can be highlighted automatically for the user to analyze. A quantified error measure can be generated that shows the error per frame or per segment between the post-stent lumen profile and the pre-stent target profile. This error measure can help the user select a suitable sized balloon when performing post stenting expansion. This error measure can include the distance by which the post-stent lumen profile and the pre-stent target profile differ.

In one embodiment, the stent profile or stent planning software uses the predicted VFR or FFR or other intravascular parameter in the pre-stent planning phase and compares it with the VFR or FFR or other intravascular parameter achieved post stent. Difference measurements such as FFR predicted—FFR after stenting can also be displayed to guide a user with respect to stent deployment related changes. If these parameters are close in value, than the stenting helped achieve the predicted result, if they differ significantly, restenting or further inflation may be needed. If the comparison shows that changes to the level of stent expansion are needed, the user interface can automatically provide guidance by identifying the region for ballooning on the image of the vessel.

The system can also display the amount of improvement in the VFR value and can further assist the user in the post-stent analysis phase. The occurrence of jailed sidebranches can be displayed by comparing pre and post segment image data and be displayed using an indicator in the event that such jailing necessitates moving the deployed stent.

The pre-stent profile is used to compare with the post stent lumen because any stent profile computed using only the post-stent pullback will be unable to take into account side branches that were jailed or blocked during stent deployment.

An exemplary workflow by which an intravascularly imaged blood vessel can be used for stent placement, selection, and expansion level evaluation is described below. If the distal and proximal reference frames are in the same segment, the stent profile is a linear interpolation between the distal and proximal reference frames.

Pre-stent planning: Physician decides on the segment of blood vessel, with a lesion or other stenosis, to stent and the stent size using the stent planning tool which can include a user interface display such as shown in FIG. 3. The selection of the references specifies the range of stent sizes possible. A first user selected reference R1 is shown on the left or distal side of the interface. A second user selected reference R2 is shown on the right or proximal side of the interface. This process is performed using one or more user interfaces that can include displays and metrics relating to one or more intravascular data sets. The target stent profile based on user provided reference frames TSP is shown as narrowing relative to the lumen profiles contours with an upper and lower boundary shown by the horizontal lines. The lumen profile LP is shown on either side of the target stent plan along the center of the vessel with the top and bottom counters bounded by the TSP such as shown in FIG. 3.

These datasets can include an OCT or IVUS data set obtained during a pullback through the vessel. Four side branches SB1-SB4 are shown in the image of the blood vessel in FIG. 3. The lumen is shown as a dark central region with the distal end on the left and proximal end on the right. The dotted vertical line corresponds to MLA. The decision on stent placement can be based on VFR or measured FFR. The predicted VFR (VFRp), the stent length and the target stent profile are generated in response to the selection of the reference frames. These values can be compared using the expected VFR or FFR during planning and the measured value achieved after stent deployment to assess the effect of the stent in the vessel and the need for further inflation or re-stenting.

Post-stent analysis: after the stent has been deployed, such as shown in the interface or display representation of FIG. 4, a new pullback is acquired, which collects intravascular data relative to the blood vessel and the newly deployed stent. As shown by the new pullback, in contrast with FIG. 3, in the second pullback shown in FIG. 4, two side branches have been blocked, SB1 and SB4, after stenting and only two were detected, SB2 and SB4. In one embodiment, the stent profile analysis software automatically identifies the stented region using the stent detection feature. The stented region's lumen profile LP is displayed with the target stent profile TSP overlaid as shown in FIG. 5.

A shown, in FIG. 5, the VFR value obtained after stenting during a second data collection session such as an OCT or IVUS pullback is displayed along with the VFRp (predicted) from the pre-stent planning phase. If the VFR post-stent is less than the VFRp from the pre-stent planning phase, then the stent deployment was below the desired target, if it is greater than VFRp, then the stent deployment successfully met the target VFR. These diagnostic differential measurements using pullbacks before and after stent deployment facilitates assessment of what if any changes should be made relative to the stented vessel and the associated stent or stents.

As shown, in FIG. 5, the lumen profile is shown with the planned pre-stent target profile shown as a dotted line. The stent profile is automatically placed over the region of the lumen profile LP that corresponds to the detected stent struts. A longitudinal view of the detected stent struts is shown in the bottom panel of the FIG. 5. In FIG. 5, the stent is underinflated relative to the target stent profile as shown. The target stent profile includes the upper and lower tapered boundaries shown by the dotted lines in FIG. 5. This follows because the detected struts of the stent identified by the image processing pipeline do not extent to the horizontal lines shown. FIG. 5 shows a representation of the blood vessel segment selected by the proximal and distal references that includes a schematic display of the stent and the target stent profile. The interface can include an image of the stent which can be viewed from different angles in the bottom panel. One or more of the panels of the user interface display of FIG. 5, all of which need not be displayed together, can help a user decide whether to inflate, move, or leave a stent in place following a stent deployment.

Figure 6:
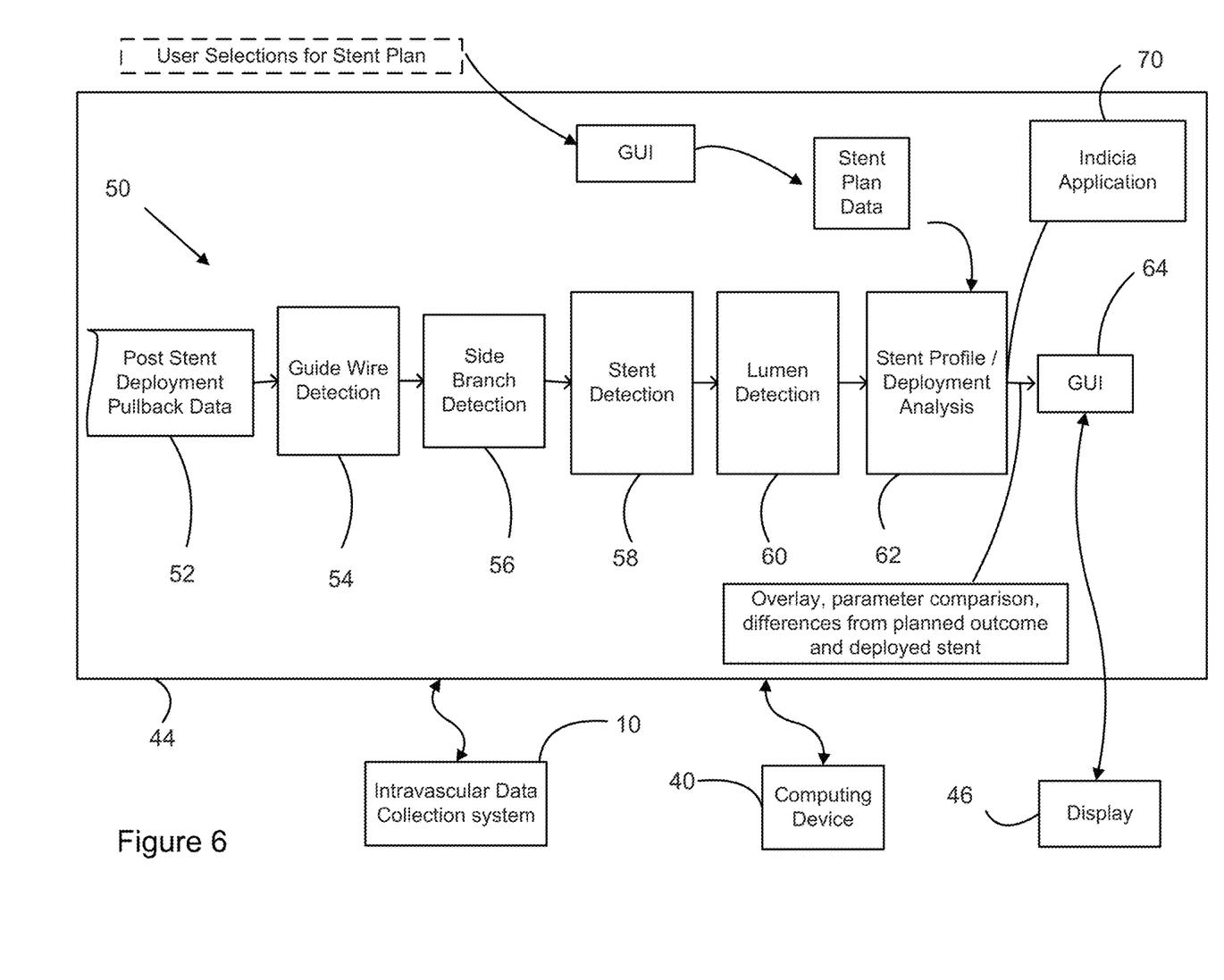
FIG. 6 is a schematic diagram of intravascular data processing software modules or components suitable for receiving data obtained relative to a vessel segment and to generate outputs and constraints suitable to implement methods disclosed herein.

An exemplary image processing pipeline 50 for transforming collected OCT data into two dimensional and three dimensional views of blood vessels and stents and comparing profiles relative to stent deployment is depicted in FIG. 6. The image data processing pipeline or any of the methods described herein are stored in memory and executed using one or more computing devices such as a processor, device, or other integrated circuit. In one embodiment, the computing device 40 includes or accesses software modules or programs 44, such as a side branch detection module, a guide wire detection module, a lumen detection module, stent deployment analysis software such as software 9 of FIG. 1, and other software modules. The software modules or programs 44 can include an image data processing pipeline or component modules thereof and one or more graphical user interfaces (GUI).

As shown, in FIG. 6, a display 46 can also be part of the system 10 for showing information such as cross-sectional and longitudinal views of a blood vessel generated using collected intravascular data such the vessel segments views and profiles in FIGS. 3, 4, and 5 and as otherwise described herein. This information 47 can be displayed using one or more graphic user interface(s) (GUI). In addition, this information 47 can include, without limitation, cross-sectional scan data, longitudinal scans, lumen profiles, VRR values, FFR values, stents, areas of malapposition, lumen border, jailed side branches, and other images or representations of a blood vessel or the underlying distance measurements obtained using an system 10 and data collection probe. The computing device 40 can also include software or programs 44, which can be stored in one or more memory devices, configured to identify target stent profiles, lumen countours, and deviations between the stent plan and outcome of a deployed stent and other blood vessel features such as with text, arrows, color coding, highlighting, contour lines, or other suitable human or machine readable indicia.

Once the OCT data is obtained with a probe and stored in memory; it can be processed to generate information such as a cross-sectional, a longitudinal, and/or a three-dimensional view of the blood vessel along the length of the pullback region or a subset thereof. These views can be depicted as part of a user interface as shown in FIGS. 3, 4 and 5. The images of the blood vessel generated using the distances measurements obtained from the OCT system provide information about the blood vessel and objects disposed therein.

As shown, the pipeline can receive post stent deployment pullback data 52 which would come after an initial pullback to image a blood vessel. User selections can be received via a GUI and the stent plan data can be transferred to stent profile or stent deployment analysis software such as software 9 in FIG. 1. The guide wire 54, side branch detection 56, stent detection 58, and lumen detection modules can operate on the post stent deployment pullback data which may be collected scan lines. The software 62 can perform various steps as described herein such overlying of profiles, parameter comparison (VFR before and after stenting, for example), and differences from the stent plan and the results of stenting the vessel.

Figure 7:
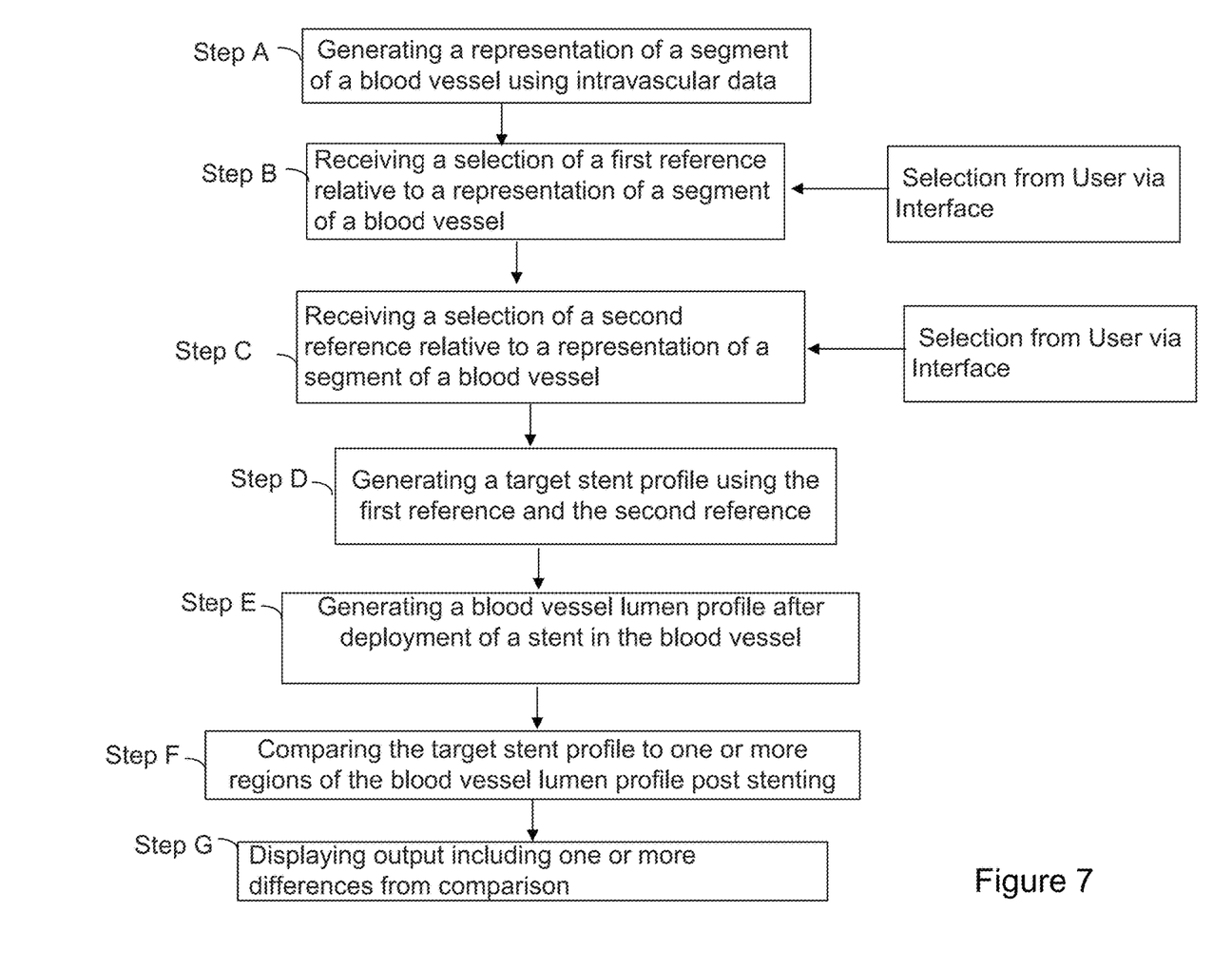
FIG. 7 is a flow chart depicting an exemplary method to evaluate a deployed stent using intravascular data collection according to an illustrative embodiment of the disclosure.

FIG. 7 shows an exemplary process flow for performing a diagnostic evaluation relative to a deployed stent. In one embodiment, the method includes steps A to E or a subset thereof with one or more user selections from an intravascular imaging system. In one embodiment, Step A includes generating a representation of a segment of a blood vessel using intravascular data. In one embodiment, Step B includes receiving a selection of a first reference relative to a representation of a segment of a blood vessel. The first and second references can include a frame or other portion of an intravascular segment representation.

These references are generated by a user interface which communicates signals or command instructions to the software 9 or other software components described herein. In one embodiment, Step C includes receiving a selection of a second reference relative to a representation of a segment of a blood vessel. In one embodiment, Step D includes generating a target stent profile using the first reference and the second reference. In one embodiment, Step E includes generating a blood vessel lumen profile after deployment of a stent in the blood vessel. In one embodiment, Step F includes comparing the target stent profile to one or more regions of the blood vessel lumen profile. In one embodiment, Step G includes displaying output including one or more differences from comparison.

An OCT image, such as the longitudinal image in the bottom panel with the detected stents struts FIG. 5 are typically acquired one scan line at a time. A sequence of samples along a ray originating at the catheter center to the maximum imaging depth is referred to as a scan line. Thus, a given scan line can correspond to a one-dimensional cue or indicia of a stent strut or stent portion. A cross-sectional image is formed by a collection of scan lines as the probe rotates.

As shown in FIGS. 1 and 2, the probe collects data during a pullback with respect to stenotic regions, blood vessel walls, and stent struts. The optical data enters the probe via a probe tip in one embodiment. The probe tip can include beam directors such as lenses or reflectors or combinations thereof are part of the probe and used to direct the beam on to the vessel wall. The probe tip also receives the scattered light that returns from the vessel wall.

In one embodiment, for non-overlapping stents, a stent strut is one point in the collection of points for a given scan line. A cross-sectional image can be formed from a set of scan lines collected as the probe rotates. Further, to image a segment of an artery or other vessel, the catheter is moved longitudinally while rotating. In this way, the probe acquires a set of cross-sectional images in a spiral pattern.

The system and software-based method described herein can process frames of optical coherence tomography data obtained with respect to a blood vessel such that a stent disposed in the blood vessel can be evaluated or otherwise characterized. In one embodiment, each cross-sectional image can constitute a frame of OCT image data. For example, in one embodiment such a stent is identified on a graphic user interface showing a three-dimensional or two-dimensional image of the blood vessel generated using collected OCT data.

The software modules and stented vessel expansion evaluation and display features described herein can be implemented using a non-transitory computer-readable storage medium. In one embodiment, the non-transitory computer-readable storage medium stores a program that, when executed by a computing device, causes the computing device to perform a method for processing or otherwise operating upon intravascular image data and intravascular parameters. Each method can include one or more of the steps outlined herein.

Non-Limiting Software Features and Embodiments for Implementing Stent Planning and Post-Deployment Diagnostic Methods and Systems The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" "overlaying" or "searching" or "detecting" or "measuring" or "calculating" or "comparing" "generating" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, detecting lumen borders, detecting stent struts, comparing measured perpendicular distances relative to set thresholds, and otherwise performing image comparison, signal processing, artifact removal, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, IVUS scan data, interferometer signal data, target stent profiles, post-stent deployment lumen profiles and images, side branch locations, side branch diameters, jailed side branches, pre-stenting FFR values, post-stenting FFR values, and other pre and post stenting values and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. The term "about" refers to a ±10% variation from a quantitative value. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of evaluating stent deployment in a blood vessel comprising:
    generating, using one or more computing devices, a first representation of a segment of the blood vessel using a first set of intravascular data obtained with respect to the blood vessel;
    receiving a selection of a first reference relative to the first representation of the segment of the blood vessel;
    receiving a selection of a second reference relative to the first representation of the segment of the blood vessel;
    generating a target stent expansion profile, using one or more computing devices, based upon the first reference and the second reference;
    generating, using the one or more computing devices, a second representation of a segment of the blood vessel using a second set of intravascular data obtained with respect to the blood vessel, wherein the second set of intravascular data is obtained after deployment of a stent in the blood vessel;
    generating, using the one or more computing devices based on the second set of intravascular data, a blood vessel lumen profile after deployment of the stent in the blood vessel;
    comparing the target stent expansion profile to one or more regions of the blood vessel lumen profile; and
    generating one or more outputs using a user interface comprising one or more differences resulting from comparing the target stent expansion profile to the one or more regions; and
    automatically identifying regions of stent over expansion or stent under expansion relative to one or more blood vessel representations.

2. The method of claim 1 wherein the one or more outputs are a visual depiction of the target stent expansion profile overlapping one or more regions of the blood vessel lumen profile.

3. The method of claim 1 wherein the one or more outputs is a comparative metric of a change in a parameter measured or calculated relative to the segment of the blood vessel.

4. The method of claim 3 wherein the parameter is selected from the group consisting of a fractional flow reserve, a flow rate, a vascular resistance ratio, a virtual fractional flow reserve, a simulated fractional flow reserve, a measured fractional flow reserve, and a pressure measurement.

5. The method of claim 1 wherein the first set of intravascular data is obtained during a first optical coherence tomography imaging session.

6. The method of claim 1 wherein the step of generating an output comprises displaying one or more outputs indicative of a correlation or goodness of fit between the target stent expansion profile and the one or more regions of the blood vessel lumen profile.

7. The method of claim 1 further comprising generating and displaying a difference between a post-stent lumen profile and a pre-stent target expansion profile or a value correlated with the difference on a per frame or per segment basis.

8. A method of evaluating stent deployment in a blood vessel comprising:
    generating, using one or more computing devices, a first representation of a segment of the blood vessel using a first set of intravascular data obtained with respect to the blood vessel;
    receiving a user selection of a first reference, from a user interface displaying the first representation, relative to the first representation of the segment of the blood vessel;
    receiving a user selection of a second reference, from a user interface displaying the first representation, relative to the first representation of the segment of the blood vessel;
    generating a target stent expansion profile, using one or more computing devices, based upon the first reference and the second reference;
    generating, using the one or more computing devices, a second representation of a segment of the blood vessel using a second set of intravascular data obtained with respect to the blood vessel, wherein the second set of intravascular data is obtained after deployment of a stent in the blood vessel;
    generating, using the one or more computing devices based on the second set of intravascular data, a blood vessel lumen profile after deployment of the stent in the blood vessel;
    determining a predicted fractional flow reserve and a target fractional flow reserve in response to the user selected references;
    displaying the blood vessel lumen profile; and
    displaying one or both of the predicted fractional flow reserve and the target fractional flow reserve.

9. The method of claim 8 further comprising
    comparing the target stent expansion profile to one or more regions of the blood vessel lumen profile; and
    generating an output using a user interface comprising one or more differences resulting from comparing the target stent expansion profile to the one or more regions.

10. The method of claim 9 wherein the step of generating an output comprises displaying one or more outputs indicative of a correlation or goodness of fit between the target stent expansion profile and the one or more regions of the blood vessel lumen profile.

11. The method of claim 9 further comprising generating and displaying a difference between a post-stent lumen profile and a pre-stent target expansion profile or a value correlated with the difference on a per frame or per segment basis.

12. The method of claim 8 wherein the first set of intravascular data is obtained during a first optical coherence tomography imaging session, wherein the blood vessel is an artery.

* * * * *